(12) United States Patent
Jurisson et al.

(10) Patent No.: US 9,593,052 B2
(45) Date of Patent: Mar. 14, 2017

(54) ARSENIC COMPLEXES FOR POTENTIAL DIAGNOSTIC APPLICATIONS

(71) Applicants: Silvia S. Jurisson, Columbia, MO (US); Cathy S. Cutler, Columbia, MO (US); Donald E. Wycoff, Columbia, MO (US); Anthony J. DeGraffenreid, Columbia, MO (US)

(72) Inventors: Silvia S. Jurisson, Columbia, MO (US); Cathy S. Cutler, Columbia, MO (US); Donald E. Wycoff, Columbia, MO (US); Anthony J. DeGraffenreid, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 14/958,185

(22) Filed: Dec. 3, 2015

(65) Prior Publication Data
US 2016/0083408 A1 Mar. 24, 2016

Related U.S. Application Data

(63) Continuation-in-part of application No. 13/969,196, filed on Aug. 16, 2013, now abandoned.

(60) Provisional application No. 61/684,421, filed on Aug. 17, 2012.

(51) Int. Cl.
| | |
|---|---|
| *A61K 51/00* | (2006.01) |
| *A61M 36/14* | (2006.01) |
| *C07B 59/00* | (2006.01) |
| *C07F 9/74* | (2006.01) |

(52) U.S. Cl.
CPC ............ *C07B 59/004* (2013.01); *C07F 9/743* (2013.01); *C07F 9/74* (2013.01)

(58) Field of Classification Search
None
See application file for complete search history.

(56) References Cited

U.S. PATENT DOCUMENTS

| | | | |
|---|---|---|---|
| 3,883,650 | A | 5/1975 | Friedheim et al. |
| 4,514,390 | A | 4/1985 | Friedheim |
| 5,459,263 | A | 10/1995 | Floc'h et al. |
| 7,803,350 | B2 | 9/2010 | Lee et al. |
| 2005/0118099 | A1 | 6/2005 | Braslawsky et al. |
| 2011/0229929 | A1 | 9/2011 | Beaulieu et al. |

OTHER PUBLICATIONS

Hamilton, C. S., and Morgan, J. F., "The Preparation of Aromatic Arsonic and Arsinic Acids by the Bart, Bechamp, and Rosenmund Reactions," in Organic Reactions, Roger Adams, ed., John Wiley and Sons, 1944, pp. 415-454.*
Ruddy A.W., (1940) "The Synthesis and Properties of Fluorinated Organic Arsenicals" (Doctoral dissertation) University of Maryland. Retrieved from http://drum.lib.umd.edu/bitstream/handle/1903/17485/DP70018.pdf?sequence=1.*
Shehata et al. (J. Radioanal. Nucl. Chem. 2011, 287, 435-442).*
Shaikh, T.A., (2007) "New Developments in Cyclized Arsenic and Antimony Thiolates" (Doctoral dissertation) University of Kentucky. Retrieved from http://uknowledge.uky.edu/cgi/viewcontent.cgi?article=1497&context=gradschool_diss.*
Botterell et al., "Use of Radioactive Arsenic (As74) in the Diagnosis of Supratentorial Brain Tumors," The Canadian Medical Association Journal, 1961, pp. 1321-1328, vol. 85, No. 25.
Bullard et al., "Phenylarsonic Acid," Organic Syntheses Coll., 1943, pp. 494, vol. 15.
Cutler et al., "Radiometals for Combined Imaging and Therapy," Chemical Reviews, 2013, pp. 858-883, vol. 113.
Gibaud et al., "(2-Phenyl-[1,3,2]dithiarsolan-4-y1)-methanol derivatives show in vitro antileukemic activity," Journal of Organometallic Chemistry, 2006, pp. 1081-1084, vol. 691.
Jennewein et al., "Vascular Imaging of Solid Tumors in Rats with a Radioactive Arsenic-Labeled Antibody that Binds Exposed Phosphatidylserine," Clinical Cancer Research, Prognosis, 2008, pp. 1377-1385, vol. 14, No. 5.
Jennewein et al., "Arsenic enhances cancer imaging," Clinical Cancer Research, 2008, 2 pages.
Jurisson et al., "Separation Methods for High Specific Activity Radioarsenic," American Institute of Physics, 2012, pp. 215-217.
Lewis et al., "Organic Syntheses," John Wiley & Sons Inc., 1923, vol. 3, pp. 13.
Office Action related to U.S. Appl. No. 13/969,196, dated Apr. 1, 2015, 11 pages.
Office Action related to U.S. Appl. No. 13/969,196, dated Sep. 3, 2015, 12 pages.
Park et al., "Noninvasive Imaging of Cell Death Using an Hsp90 Ligand," Journal of the American Chemical Society, 2011, pp. 2832-2835, vol. 133.
Shi et al., "The Role of Arsenic-Thiol Interactions in Metalloregulation of the ars Operon," The Journal of Biological Chemistry, 1996, pp. 9291-9297, vol. 271, No. 16.
Wu et al., "Bioengineering Single Crystal Growth," Journal American Chemical Society, 2010, pp. 2832-2835, vol. 133.
Nhittaker et al., "An Experimental Investigation of the 'Ring Hypothesis' of Arsenical Toxicity," Journal Biol. Chem, 1947, pp. 56-62, vol. 41.
Emran et al., "New Trends in Radiopharmaceutical Synthesis, Quality Assurance and Regulatory Control," A.M. Emran, Plenium Press, New York, 1991, pp. 153-168.
Phenylarsonic acid Wikipedia 2015.

\* cited by examiner

*Primary Examiner* — Michael G Hartley
*Assistant Examiner* — Melissa Perreira
(74) *Attorney, Agent, or Firm* — Polsinelli PC

(57) ABSTRACT

The present invention provides radioactive arsenic complexes useful in diagnostic and therapeutic applications and methods for forming those arsenic complexes.

20 Claims, No Drawings

ARSENIC COMPLEXES FOR POTENTIAL DIAGNOSTIC APPLICATIONS

CROSS REFERENCE TO RELATED APPLICATIONS

This application is a continuation-in-part of U.S. application Ser. No. 13/969,196, filed Aug. 16, 2013, which claims the benefit of U.S. Provisional Application No. 61/684,421, filed Aug. 17, 2012, each of the disclosures of which is hereby incorporated by reference in its entirety.

GOVERNMENTAL RIGHTS

This invention was made with government support under Grant No. DE-SC0003851 and DE-SC0010283 awarded by the United States Department of Energy, and under Training Grant No. ST32-EB004822 awarded by the National Institute of Biomedical Imaging and Bioengineering (NIBIB) at the National Institutes of Health (NIH), an agency of the United States Department of Health and Human Services. The government has certain rights to the invention.

FIELD OF THE INVENTION

The present invention generally relates to arsenic complexes, especially to radioactive arsenic complexes useful in diagnostic and therapeutic applications and to methods for forming those complexes.

BACKGROUND OF THE INVENTION

Currently, positron emission tomography (PET) imaging relies upon $^{18}$F as the positron emitter, typically in the form of fluorodeoxyglucose (FDG), which is metabolized by active body tissue. With a short half-life of only 1.8 hours, radiopharmaceuticals containing $^{18}$F must be synthesized immediately before administration to patients near the cyclotron source of the element. Such a short half-life makes it difficult to use with antibodies and does not permit these radiopharmaceuticals to be used in radiotherapy.

Because of their significantly longer half-life than $^{18}$F, arsenic radioisotopes permit a much wider range of radiopharmaceuticals, including labeling biological vectors. As such, radiotherapeutic agents can then be developed for targeting a variety of diseases using arsenic radiolabeled biomolecules, adding to the arsenal of potential cancer therapeutics.

What is needed then are more reliable methods for preparing arsenic radioisotopes and compounds containing those radioisotopes.

SUMMARY OF THE INVENTION

Briefly, therefore, one aspect of the present disclosure encompasses processes for preparing radiolabeled phenylarsonic acid, $C_6H_5AsO_3H_2$, from radiolabeled arsenous acid or no-carrier added arsenic acid. The phenylarsonic acid may be used as a precursor for radiolabeled arsenic complexes for diagnostic or therapeutic nuclear medicine. These arsenic complexes are formed by reaction between the radiolabeled phenylarsonic acid and a sulfur-containing reagent, such as a monothiol or a dithiol.

Another aspect of invention, the disclosure provides a composition comprising a compound of Formula (I):

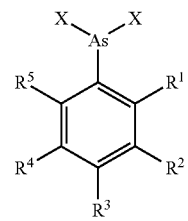

Formula (I)

wherein arsenic is radioactive;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic, and heteroaromatic rings;

X represents ligand atoms wherein X is chosen from oxygen, sulfur, nitrogen, and halide;

X may be further substituted by hydrogen, hydrocarbyl or substituted hydrocarbyl. In another aspect of the disclosure, there is provided a composition comprising Formula (II):

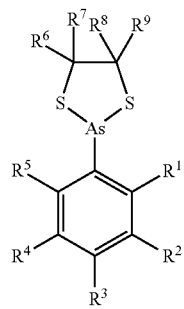

Formula (II)

wherein arsenic is radioactive;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic and heteroaromatic rings; and $R^6$, $R^7$, $R^8$, and $R^9$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl and substituted hydrocarbyl rings and aromatic and heteroaromatic rings.

In yet another aspect of the disclosure, there is provided a composition comprising Formula (III):

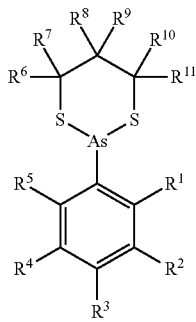

Formula (III)

wherein arsenic is radioactive;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl rings, aromatic and heteroaromatic rings; and $R^6$, $R^7$, $R^8$, $R^9$, $R^{10}$, and $R^{11}$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic and heteroaromatic rings.

In other aspects of the disclosure, there is provided a radiopharmaceutical comprising Formula (I), (II), or (III):

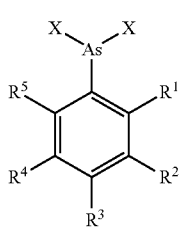

Formula (I)

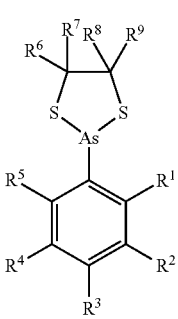

Formula (II)

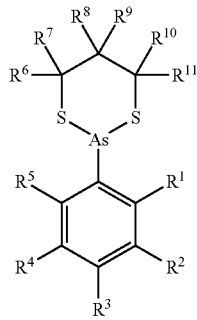

Formula (III)

wherein arsenic is radioactive;

X represents ligand atoms wherein X is chosen from oxygen, sulfur, nitrogen, and halides;

X may be further substituted with hydrogen, hydrocarbyl or substituted hydrocarbyl;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic and heteroaromatic rings; and $R^6$, $R^7$, $R^8$, $R^9$, $R^{10}$, and $R^{11}$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl and substituted hydrocarbyl rings and aromatic and heteroaromatic rings.

In still other aspects of the disclosure, there is provided a method for producing radiolabeled phenylarsonic acid. The method comprises contacting a radiolabeled no-carrier added arsenic acid with a monothiol to form a first solution; and contacting the first solution with a copper-based catalyst and a phenyldiazonium salt to give a second solution comprising the radiolabeled phenylarsonic acid.

Other features and iterations of the invention are described in more detail below.

DETAILED DESCRIPTION OF THE INVENTION

The present invention provides arsenic complexes containing radioactive arsenic as well as processes for preparing those arsenic complexes.

(I) Compounds

In general, the disclosure provides a composition comprising a compound of Formula (I):

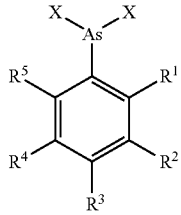

Formula (I)

wherein arsenic is radioactive;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic, and heteroaromatic rings;

X represents ligand atoms wherein X is chosen from oxygen, sulfur, nitrogen, and halides;

X may be further substituted by hydrogen, hydrocarbyl or substituted hydrocarbyl.

In some embodiments, the arsenic may be chosen from $^{72}$As or $^{77}$As. In other embodiments, the $R^3$ may be $NH_2$. In still other embodiments, $R^3$ may be $NH_2$, and $R^1$, $R^2$, $R^4$, and $R^5$ are hydrogen. In some iterations, each X may be sulfur and may be further substituted by hydrogen, hydrocarbyl or substituted hydrocarbyl. In other iterations, one or both X may be further substituted by carboxylic acids, phenyl groups or amines. In still other iterations, one or both X may be further substituted by $CH_2COOH$. In some other iterations, one or both X may be further substituted by $CH_2Ph$. In other iterations, one or both X may be further substituted by $CH_2CH_2NH_2$. In some embodiments, the composition may be isolated.

In another aspect of the disclosure, there is provided a composition comprising Formula (II):

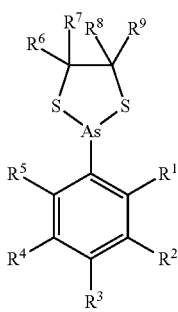

Formula (II)

wherein arsenic is radioactive;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic and heteroaromatic rings; and $R^6$, $R^7$, $R^8$, and $R^9$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl and substituted hydrocarbyl rings and aromatic and heteroaromatic rings.

In some embodiments, the arsenic may be chosen from $^{72}$As or $^{77}$As. In other embodiments, $R^3$ may be $NH_2$, and $R^1$, $R^2$, $R^4$, and $R^5$ may each be hydrogen. In still other embodiments, $R^6$, $R^7$, $R^8$, and $R^9$ may each be hydrogen. In some iterations, one or more of $R^6$, $R^7$, $R^8$, and $R^9$ may be substituted with a $C_1$-$C_{10}$ carboxylic acid. In other iterations, $R^6$ and $R^8$ may be substituted by COOH. In some other iterations, $R^7$ and $R^9$ may be substituted by hydrogen. In still other iterations, one of $R^6$, $R^7$, $R^8$, or $R^9$ may be substituted by a linear $C_1$-$C_5$ carboxylic acid. In some embodiments, $R^6$, $R^7$, $R^8$, or $R^9$ may be substituted such to form a fused ring system with one or more hydrocarbyl, substituted hydrocarbyl, aromatic or heteroaromatic rings. In other embodiments, the composition may be isolated.

In yet another aspect of the disclosure, there is provided a composition comprising Formula (III):

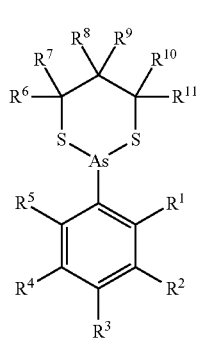

Formula (III)

wherein arsenic is radioactive;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl rings, aromatic and heteroaromatic rings; and $R^6$, $R^7$, $R^8$, $R^9$, $R^{10}$, and $R^{11}$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic and heteroaromatic rings.

In some embodiments, the arsenic may be chosen from $^{72}$As or $^{77}$As. In other embodiments, $R^3$ may be $NH_2$, and $R^1$, $R^2$, $R^4$, and $R^5$ may each be hydrogen. In some iterations, $R^6$, $R^7$, $R^8$, $R^9$, $R^{10}$, and $R^{11}$ may each be hydrogen. In other iterations, one or more of $R^6$, $R^7$, $R^8$, $R^9$, $R^{10}$, and $R^{11}$ may be substituted with a $C_1$-$C_{10}$ carboxylic acid. In some other iterations, one or more of $R^6$, $R^8$, or $R^{10}$ may be substituted by COOH. In still other iterations, one of $R^6$, $R^7$, $R^8$, $R^9$, $R^{10}$, and $R^{11}$ may be substituted by a $C_1$-$C_5$ carboxylic acid. In some embodiments, two or more of $R^6$, $R^7$, $R^8$, $R^9$, $R^{10}$, and $R^{11}$ may be substituted such to form a fused ring system with one or more hydrocarbyl, substituted hydrocarbyl, aromatic or heteroaromatic ring systems. In other embodiments, the composition may be isolated.

In other aspects of the disclosure, there is provided a radiopharmaceutical comprising Formula (I), (II), or (III):

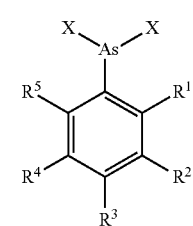

Formula (I)

-continued

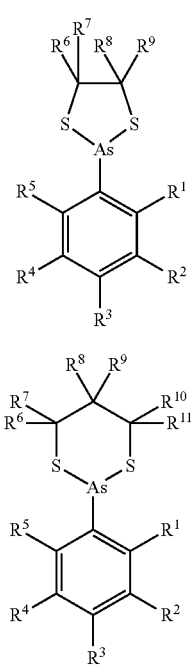

Formula (II)

Formula (III)

wherein arsenic is radioactive;

X represents ligand atoms wherein X is chosen from oxygen, sulfur, nitrogen, and halides;

X may be further substituted with hydrogen, hydrocarbyl or substituted hydrocarbyl;

$R^1$, $R^2$, $R^3$, $R^4$, and $R^5$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl, substituted hydrocarbyl, aromatic and heteroaromatic rings; and $R^6$, $R^7$, $R^8$, $R^9$, $R^{10}$, and $R^{11}$ are independently selected from hydrogen, hydrocarbyl, substituted hydrocarbyl, amines, substituted amines, halogens, hydroxyl, carboxylic acid, thiol, or nitro groups or are joined together to form one or more fused ring systems selected from hydrocarbyl and substituted hydrocarbyl rings and aromatic and heteroaromatic rings.

In some embodiments, the arsenic may be chosen from $^{72}$As or $^{77}$As. In other embodiments, $R^3$ may be $NH_2$, and $R^1$, $R^2$, $R^4$, and $R^5$ may each be hydrogen. In some iterations, $R^6$, $R^7$, $R^8$, $R^9$, $R^{10}$, and $R^{11}$ may be independently selected from hydrogen, hydrocarbyl, and substituted hydrocarbyl. In other iterations, $R^6$, $R^7$, $R^8$, $R^9$, $R^{10}$, and $R^{11}$ may be independently selected from hydrogen, carboxylic acid, and $C_1$-$C_{10}$ carboxylic acids.

In an exemplary embodiment, the compound of Formula (I), (II), or (III) may be conjugated to a peptide. The peptide may be, for example, bombesin or a site-specific antibody.

(a) Radioactive Arsenic

The compounds of Formulas (I), (II), and (III) contain radioactive arsenic. Radioactive isotopes of arsenic include $^{68}$As, $^{68m}$As, $^{69}$As, $^{70}$As, $^{70m}$As, $^{71}$As, $^{72}$As, $^{73}$As, $^{74}$As, $^{75m}$As, $^{76}$As, $^{76m}$As, $^{77}$As, $^{77m}$As, $^{78}$As, $^{79}$As, and $^{79m}$As. In some embodiments, the arsenic isotope may be relatively long-lived. For example, the isotope may have a half-life of at least one day. Examples of relatively long-lived radioactive isotopes of arsenic include $^{68}$As, $^{69}$As, $^{70}$As, $^{71}$As, $^{72}$As, $^{73}$As, $^{74}$As, $^{76}$As, $^{77}$As, $^{78}$As, and $^{79}$As. In exemplary embodiments, the radioisotope of arsenic may be $^{72}$As or $^{77}$As.

Arsenic radioisotopes may be selected for their desirable nuclear properties, such as a half-life that is sufficiently long to permit chemical derivation, radiodiagnostic imaging, and/or radiotherapy, but short enough that the radionuclide can clear the patient's body within a suitable time after administration. Arsenic radioisotopes may also be selected that undergo a high percentage of beta decay, rather than other modes of radioactive decay, such as electron capture (EC). A high percentage of positron ($\beta^+$) decay is desirable for positron emission tomography (PET), which relies upon positron emission of the radioisotope for imaging, and a high percentage of gamma emission for single-photon emission computed tomography (SPECT) imaging. Another desirable property of arsenic radioisotopes is a maximum energy for positron emission ($E\beta_{max}$) that permits image resolution similar to images acquired from an $^{18}$F-labeled compound. The properties for some exemplary arsenic radioisotopes are shown below in Table 1:

TABLE 1

Properties of exemplary arsenic radioisotopes

| Property | $^{70}$As | $^{71}$As | $^{72}$As | $^{74}$As | $^{76}$As | $^{77}$As |
|---|---|---|---|---|---|---|
| Half-life ($t_{1/2}$) | 52.5 min | 2.7 days | 1.1 days | 17.8 days | 1.6 days | 38.8 h |
| Mode of decay (%) | $\beta^+$ (100%) | EC (68%); $\beta^+$ (32%) | $\beta^+$ (87.8%); EC (12.2%) | EC (66%); $\beta^+$ (29%) | $\beta^-$ (100%) | $\beta^-$ (100%) |
| $E\beta_{max}$ (MeV) | 1.44 | 2.01 | 2.5 | 0.94 | 2.94 | |

* EC = electron capture (b) Biological Vectors

In vivo stable compounds of radiolabeled arsenic complexes linked to biological vectors enable a new class of PET imaging agents to be developed for a wide range of medical applications. For example, the half-life of $^{72}$As is 26 hours, permitting its use as a label for peptides and possibly antibodies giving specificity in target imaging. In another example, in vivo stable compounds of $^{77}$As linked to biological vectors would enable a new class of radiotherapeutic agents to be developed for a wide range of medical applications. For instance, $^{77}$As would allow simultaneous radiotherapy and SPECT imaging by emission and detection of 239-keV gamma radiation. In other examples, the annihilation of emitted positrons from a radioactive arsenic species may produce gamma radiation which can be detected through SPECT imaging.

In some embodiments, the biological vector may be a peptide. In various embodiments, the peptide has a relatively low molecular weight and rapid in vivo blood clearance. Non-limiting examples of peptides include bombesin, site-directed antibodies, neuromedin B, neuromedin N, neuromedin S, neuromedin U; angiotensin, calcitonin gene-related peptide, carnosine, cocaine and amphetamine regulated transcript, delta sleep-inducing peptide, FMRF-amide (Phe-Met-Arg-Phe), galanin, galanin-like peptide, gastrin-releasing peptide, neuropeptide S, neuropeptide Y, neurophysins, neurotensin, pancreatic polypeptide, pituitary adenylated cyclase-activating peptide, RVD-Hpα, VGF; a kinin, such as cholecystokinin, bradykinin or tachykinin, for example substance P, neurokinin A, neurokinin B, kassinin, or physalaemin; a dynorphin, such as dynorphin A or dynorphin B; an endorphin, such as beta-endorphin, alpha-endorphin, gamma-endorphin, α-neo-endorphin, or β-neo-endorphin; an encephalin, such as Met-encephalin or Leu-encephalin; adrenorphin, amidorphin, leumorphin, nociception, oriorphin, spinorphin; or a peptide hormone, such as prolactin, adrenocorticotropic hormone (ACTH), growth hormone, vasopressin, oxytocin, atrial-natriuretic peptide (ANP), atrial-natriuretic factor (ANF), glucagon, insulin, somatostatin, or leptin. In an exemplary embodiment, the peptide bombesin, a 14-amino acid peptide originally isolated from the skin of the oriental fire-bellied toad (*Bombina orientalis*). Bombesin stimulates gastrin release from G cells, in particular activating the G-protein-coupled receptors BBR1, BBR2, and BBR3. In other exemplary embodiments, the peptide is a site-directed antibody; that is, an immunoglobulin designed to recognize specific targets.

(c) Downstream Applications

In some embodiments, the compound comprising Formula (I), (II) or (III) may be converted into a pharmaceutically acceptable salt. "Pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds comprising Formula (I), (II), or (III) may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine-(N-methylglucamine) and procaine. All of these salts may be prepared by conventional means from the corresponding compound by reacting, for example, the appropriate acid or base with the any compound comprising Formula (I), (II), or (III).

(d) Stereochemistry

The compound comprising any of Formulas (I), (II), or (III) may have a (−) or a (+) orientation with respect to the rotation of polarized light. More specifically, each chiral center of the arsenic complex may have an R or an S configuration.

(II) Process for Preparation of Arsenic Complexes

In still other aspects of the disclosure, there is provided a method of producing radiolabeled phenylarsonic acid. The method comprises contacting a radiolabeled arsenous acid with a carbonate to form a first solution. The first solution is contacted with a phenyldiazonium salt and a copper-based catalyst, to form a second solution comprising the labeled phenylarsonic acid.

In some embodiments, the carrier-added radiolabeled arsenous acid may be —$H_3AsO_3$, or $As(OH)_3$. In an exemplary embodiment, the carbonate may be sodium carbonate. In other embodiments, the phenyldiazonium salt may be a tetrafluoroborate salt. In some embodiments, the first solution may be heated to about 70° C. to about 90° C. In other embodiments, the copper-based catalyst may be copper(II) sulfate ($CuSO_4$), and the mole to mole ratio of arsenous acid to $CuSO_4$ may range from about 1:2 to 1:3. In an exemplary embodiment, the contact between the first solution and the phenyldiazonium salt may be conducted at about 0° C. In another exemplary embodiment, the process may further comprise neutralizing and filtering the second solution. In other embodiments, the radiolabeled phenylarsonic acid may be isolated. In an exemplary embodiment, the phenylarsonic acid may be further reacted with a monothiol or dithiol.

In still yet other aspects of the disclosure, there is provided a method of producing radiolabeled phenylarsonic acid using no-carrier added arsenic. The method comprises contacting a radiolabeled no-carrier added arsenic acid with a monothiol to form a first solution. The first solution is contacted with a copper-based catalyst and a phenyldiazonium salt to form a second solution comprising the labeled phenylarsonic acid.

In other embodiments, the radiolabeled arsenic acid is chosen from $AsO_4^{3-}$ or $H_3AsO_4$. Specifically, the radiolabeled arsenic acid is no carrier added $AsO_4^{3-}$. In an exemplary embodiment, the monothiol is ammonium thioglycolate. In other embodiments, the phenyldiazonium salt is a tetrafluoroborate salt. In some embodiments, the first solution is heated to about 50° C. to about 70° C. In other embodiments, the copper-based catalyst is copper(0) nanoparticles, and the mole to mole ratio of reaction intermediate to copper(0) nanoparticles ranges from about $1:10^5$ to about $1:10^6$. In an exemplary embodiment, the contact between the first solution and the phenyldiazonium salt is conducted at about 20° C. to about 30° C. In an exemplary embodiment, the phenylarsonic acid is further reacted with a monothiol and/or dithiol.

(a) Step A—Reaction Mixture (i) Radiolabeled Arsenic

The arsenic may be in any form, for example arsenic can exist in several oxidation states (−3, −2, −1, 0, +1, +2, +3, +4, and +5). Preferably, arsenic for use in a method of synthesis of the disclosure is in oxidation state +3 or +5, also referred to as As(III) and As(V), respectively. As used herein, when As(III) is the starting material for the reaction, the arsenic may be referred to as arsenous acid, $H_3AsO_3$, $As(OH)_3$, arsenite or As(III). Further, as used herein, when As(V) is the starting material for the reaction, the arsenic may be referred to as arsenic acid, $H_3AsO_4$, $AsO_4^{3-}$, $HAsO_4^{-2}$, arsenate or As(V). The arsenic may be any radioactive arsenic described above in Section (I)(a). Specifically, the arsenic may be $^{77}As$, $^{72}As$, or $^{76}As$.

Preferably, the arsenic is no-carrier added arsenic. By "no-carrier added", also referred to as "NCA" or "n.c.a.", is meant a preparation of a radioactive isotope which is essentially free from stable isotopes of the element in question. It is understood in the art that no-carrier added radionuclide indicates ng or less quantities of said radionuclide. Specifically, when no-carrier added arsenic is the starting material in a method of synthesis of the disclosure the oxidation state is +5 or As(V). Accordingly, the no-carrier added arsenic is arsenic acid, $H_3AsO_4$, $AsO_4^{3-}$, $HAsO_4^{-2}$, arsenate or As(V). In an exemplary embodiment, the radioactive arsenic in the no-carrier added arsenic is $^{77}As$, or $^{72}As$.

(ii) Carbonate or Monothiol

The carrier-added arsenous acid is contacted with a carbonate. Non-limiting examples of a carbonate include sodium carbonate, potassium carbonate, lithium carbonate, and magnesium carbonate. In an exemplary embodiment, the carbonate is sodium carbonate.

The amount of carbonate added to the reaction mixture can and will vary. In general, the mole:mole ratio of the arsenous acid to the carbonate may range from about 1:5 to about 1:500. In various embodiments, the molar ratio of arsenous acid to the carbonate may range from about 1:5 to about 1:10, from about 1:10 to about 1:50, from about 1:50 to about 1:100, from about 1:100 to about 1:200, from about 1:200 to about 1:300, from about 1:300 to about 1:400, or from about 1:400 to about 1:500. In one exemplary embodiment, the mole:mole ratio of the arsenous acid to carbonate may range from about 1:40 to about 1:60.

When no-carrier added arsenic acid is the starting material, the arsenic acid is contacted with a monothiol. A monothiol is any thiol that has a single SH group. Non-limiting examples of monothiols include mercaptomethylamine, mercaptoethylamine, mercaptopropylamine, mercaptobutylamine, ammonium thioglycolate, cysteine, 2-aminoethanethiol (cysteamine), coenzyme A, and glutathione. Non-limiting examples of monothiols include methanethiol, ethanethiol, 1-propanethiol, 2-propanethiol, butanethiol, tert-butyl mercaptan, penanethiol, thiophenol, 2-mercaptoacetic acid, thioacetic acid, phenylmethanthiol (benzyl mercaptan), 2-mercaptoethanol, 3-mercaptopropane-1,2-diol, furan-2-ylmethanethiol, 2-mercaptoindole, and 2-(4-methylcyclohex-3-enyl)propane-2-thiol (thioterpineol). Preferably, the monothiol is a water soluble monothiol. Specifically, the monothiol is a thioglycolate. Non-limiting examples of thioglycolates include ammonium thioglycolate, sodium thioglycolate and calcium thioglycolate. In an exemplary embodiment, the thioglycolate is ammonium thioglycolate.

In general, the mole:mole ratio of the no-carrier added arsenic acid to the monothiol may range from about $1:10^4$ to about $1:10^8$. In various embodiments, the molar ratio of no-carrier added arsenic acid to the monothiol may be about $1:10^4$, about $1:10^5$, about $1:10^6$, about $1:10^7$, or about $1:10^8$. In other embodiments, the molar ratio of no-carrier added arsenic acid to the monothiol may range from about $1:10^4$ to about $1:10^7$, about $1:10^4$ to about $1:10^6$, about $1:10^4$ to about $1:10^5$, about $1:10^5$ to about $1:10^8$, about $1:10^5$ to about $1:10^7$, about $1:10^5$ to about $1:10^6$, to about $1:10^6$ to about $1:10^8$, about $1:10^6$ to about $1:10^7$, or about $1:10^7$ to about $1:10^8$. In one exemplary embodiment, the mole:mole ratio of the no-carrier added arsenic acid to monothiol may range from about $1:10^5$ to about $1:10^7$. In another exemplary embodiment, the mole:mole ratio of the no-carrier added arsenic acid to monothiol may be about $1:10^5$.

(iii) Solvent

The reaction is generally conducted in the presence of a solvent or solvent system. The solvent may be a polar protic solvent, a polar aprotic solvent, or a nonpolar organic solvent. Non-limiting examples of suitable polar protic solvents include methanol, ethanol, isopropanol, n-propanol, isobutanol, n-butanol, s-butanol, t-butanol, formic acid, acetic acid, water, and combinations thereof. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Representative nonpolar solvents include, but are not limited to, alkane and substituted alkane solvents (including cycloalkanes), aromatic hydrocarbons, esters, ethers, ketones, and combinations thereof. Specific nonpolar solvents that may be employed include, for example, benzene, butyl acetate, t-butyl methylether, t-butyl methylketone, chlorobenzene, chloroform, cyclohexane, dichloromethane, dichloroethane, diethyl ether, ethyl acetate, fluorobenzene, heptane, hexanes, methyl ethylketone (2-butanone), methyl isobutyl ketone, pentyl acetate, propyl acetates, toluene, and combinations thereof. In an exemplary embodiment, the solvent is a polar protic solvent. For example, the solvent is water, deuterium oxide ($D_2O$), or combinations thereof. In another exemplary embodiment, the solvent is a polar aprotic solvent. For example, the solvent is acetonitrile.

In general, the volume to mass ratio of the solvent to carrier-added arsenous acid may range from about 0.001:1 to about 1:1. In various embodiments, the volume to mass ratio of the solvent to arsenous acid may range from 0.001:1 to about 0.01:1, from about 0.01:1 to about 0.1:1, or from about 0.1:1 to about 1:1. In exemplary embodiments, the volume to mass ratio of the solvent to arsenous acid may range from about 0.01:1 to about 0.05:1.

When no-carrier added arsenic acid is the starting material, in general, the volume to mass ratio of the solvent to no-carrier added arsenic acid may range from about 1:0.001 to about 1:0.0000001. In various embodiments, the volume to mass ratio of the solvent to no-carrier added arsenic acid may be about 1:0.001, about 1:0.0001, about 1:0.00001, about 1:0.000001, or about 1:0.0000001. In other embodiments, the volume to mass ratio of the solvent to no-carrier added arsenic acid may range from about 1:0.001 to about 1:0.000001, about 1:0.001 to about 1:0.00001, about 1:0.001 to about 1:0.0001, about 1:0.0001 to about 1:0.0000001, about 1:0.0001 to about 1:0.000001, about 1:0.0001 to about 1:0.00001, about 1:0.00001 to about 1:0.0000001, about 1:0.00001 to about 1:0.000001, or about 1:0.000001 to about 1:0.0000001. In exemplary embodiments, the volume to mass ratio of the solvent to no-carrier added arsenic acid may range from about 1:0.0001 to about 1:0.000001. In another exemplary embodiment, the volume to mass ratio of the solvent to no-carrier added arsenic acid may be about 1:0.000001.

(b) Step A—Reaction Conditions

In general, the reaction may be conducted at a temperature that ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100° C. to about 120° C. In an exemplary embodiment, the reaction may be conducted at a temperature of about 70° C. to about 90° C. In another exemplary embodiment, the reaction may be conducted at a temperature of about 50° C. to about 70° C. In still another exemplary embodiment, the reaction may be conducted at a temperature of about 60° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of starting material, and a significantly increased amount of reaction intermediate compared to the amounts of each present at the beginning of the reaction. In general, the reaction may proceed for about 1 minute to about 12 hours. Typically, the duration of the reaction is longer at lower reaction temperatures. In certain embodiments, the reaction may be allowed to proceed for a period of time ranging from about 1 minute to about 5 minutes, from about 5 minutes to about 10 minutes, from about 10 minutes to about 15 minutes, from about 15 minutes to about 30 minutes, from about 30 minutes to about 1 hour, from about 1 hour to about 3 hours, from about 3 hours to about 6 hours, from about 6 hours to about 9 hours, or from about 9 hours to about 12 hours. In an exemplary embodiment, the reaction may be allowed to proceed for a period of time ranging from about 30 minutes to about 1 hour.

In some embodiments, the reaction intermediate may be isolated from the reaction mixture using techniques known to those of skill in the art. Non-limiting examples of suitable techniques include precipitation, extraction, evaporation, distillation, chromatography, and crystallization. In other embodiments, the reaction intermediate may not be isolated and step (b) of the process may proceed in the same reaction pot or reactor.

The yield of the reaction intermediate can and will vary. Typically, the yield of the reaction intermediate may be at least about 40%. In one embodiment, the yield of the reaction intermediate may range from about 40% to about 60%. In another embodiment, the yield of the reaction intermediate may range from about 60% to about 80%. In a further embodiment, the yield of the reaction intermediate may range from about 80% to about 90%. In still another embodiment, the yield of the reaction intermediate may be greater than about 90%, or greater than about 95%.

(c) Step B—Reaction Mixture

The method for producing a radiolabeled phenylarsonic acid comprises contacting the solution from Step A with a copper-based catalyst. The copper catalyst may be added at the reaction temperature of Step A and then the reaction mixture may be shifted to the reaction temperature of Step B. The copper atom in the copper-based catalyst may have an oxidation state of 0, 1+, 2+, or 3+. Non-limiting examples of suitable copper-based catalysts include copper(0) nanoparticles, copper(I) bromide (CuBr), copper(I) chloride (CuC), copper(I) fluoride (CuF), copper(I) iodide (CuI), copper chromite ($Cu_2Cr_2O_5$), copper(I) oxide ($Cu_2O$), copper(I) sulfide ($Cu_2S$), copper(I) phosphate ($Cu_3(PO_4)_2$), copper(I) phosphide ($Cu_3P$), copper tetrafluoroborate ($Cu(BF_4)_2$), copper(II) bromide ($CuBr_2$), copper(II) carbide ($CuC_2$), copper(II) carbonate ($CuCO_3$), copper(II) chloride ($CuCl_2$), copper(II) fluoride ($CuF_2$), copper(II) nitrate ($Cu(NO_3)_2$), copper(II) oxide (CuO), copper(II) hydroxide ($Cu(OH)_2$), copper(II) iodide ($CuI_2$), copper(II) sulfide (CuS), copper(II) sulfate ($CuSO_4$), potassium hexafluorocuprate ($K_3CuF_6$), and cesium hexafluorocuprate ($Cs_2CuF_6$). In an exemplary embodiment, the copper-based catalyst may be copper(II) sulfate ($CuSO_4$). In another exemplary embodiment, the copper-based catalyst may be copper(0) nanoparticles.

In some embodiments, the copper-based catalyst may be the copper metal element itself. Specifically, when no-carrier added arsenic acid is the starting material, the preferred copper-based catalyst is the copper metal element itself. Specifically, the copper-based catalyst may be copper(0) nanoparticles. Additionally, the copper may be a powder or a sponge. In other embodiments, the copper may be immobilized on a solid surface or support. The copper-based catalyst may be soluble (i.e., homogeneous) or may be immobilized on a solid support (i.e., heterogeneous), for example via noncovalent or covalent bonds. In some embodiments, the solid support may be an inorganic material. Suitable inorganic materials include silicas, alumina, titania, carbondium, zirconia, activated charcoal, zeolites, clays, polymers, ceramics, and activated carbon. Suitable silicas include silicon dioxide, amorphous silica, and microporous or mesoporous silicas. In other embodiments, the solid support may be a polymer. The polymer may be a natural polymer, a synthetic polymer, a semi-synthetic polymer, or a copolymer. Non-limiting examples of polymers include agarose, cellulose, nitrocellulose, methyl cellulose, polyacrylic, polyacrylamide, polyacrylonitrile, polyamide, polyether, polyester, polyethylene, polystyrene, polysulfone, polyvinyl chloride, polyvinylidene, methacrylate copolymer, and polystyrene-vinyl chloride copolymer.

The amount of copper-based catalyst added to the reaction mixture can and will vary. In certain embodiments, when carrier added arenous acid is the starting material, the mole:mole ratio of the reaction intermediate to the copper-based catalyst may range from about 1:0.03 to about 1:3. In various embodiments, the molar ratio of reaction intermediate to the copper-based catalyst may range from about 1:0.03 to about 1:0.1, from about 1:0.1 to about 1:0.2, from about 1:0.2 to about 1:0.3, from about 1:0.3 to about 1:0.4, from about 1:0.4 to about 1:0.5, from about 1:0.5 to about 1:1, from about 1:1 to about 1:2, or from about 1:2 to about 1:3. In one exemplary embodiment, the mole:mole ratio of the reaction intermediate to copper-based catalyst may range from about 1:0.2 to about 1:0.3. In another exemplary embodiment, the copper-based catalyst is copper(II) sulfate, and the mole:mole ratio of the reaction intermediate to copper(II) sulfate may range from about 1:0.2 to about 1:0.3.

Specifically, when no-carrier added arsenic acid is the starting material, the mole:mole ratio of the reaction intermediate to the copper-based catalyst may range from about $1:10^3$ to about $1:10^8$. In various embodiments, the molar ratio of reaction intermediate to the copper-based catalyst may be about $1:10^3$, about $1:10^4$, about $1:10^5$, about $1:10^6$, about $1:10^7$, or about $1:10^8$. In other embodiments, the molar ratio of reaction intermediate to the copper-based catalyst may range from about $1:10^3$ to about $1:10^7$, about $1:10^3$ to about $1:10^6$, about $1:10^3$ to about $1:10^5$, about $1:10^3$ to about $1:10^4$, about $1:10^4$ to about $1:10^7$, about $1:10^4$ to about $1:10^6$, about $1:10^4$ to about $1:10^5$, about $1:10^5$ to about $1:10^8$, about $1:10^5$ to about $1:10^7$, about $1:10^5$ to about $1:10^6$, to about $1:10^6$ to about $1:10^8$, about $1:10^6$ to about $1:10^7$, or about $1:10^7$ to about $1:10^8$. In one exemplary embodiment, the mole:mole ratio of the reaction intermediate to copper-based catalyst may be about $1:10^5$. In another exemplary embodiment, the copper-based catalyst is copper(0) nanoparticles, and the mole:mole ratio of the reaction intermediate to copper(0) nanoparticles may be about $1:10^5$.

The method for producing a radiolabeled phenylarsonic acid further comprises contacting the solution from Step A, in the presence of a copper catalyst, with a phenyldiazonium salt to form a phenylarsonic acid. The phenyldiazonium salt may be added at the reaction temperature of Step A and then the reaction mixture may be shifted to the reaction temperature of Step B. In the phenyldiazonium salt, the phenyldiazonium cation (also referred to as benzenediazonium) is paired with a counteranion, for example a halide, such as chloride, bromide or iodide; tetrafluoroborate, nitrate, sulfate, or phosphate. In an exemplary embodiment, the counteranion is tetrafluoroborate, thus forming the tetrafluoroborate salt. In some embodiments, the phenyldiazonium is optionally substituted, for example with an amino group or a lower alkane. In exemplary embodiments, the phenyldiazonium salt is ethoxybenzendiazonium salt. When an amino-substituted phenyldiazonium salt is used, the reaction product is arsanilic acid, such as ortho-arsanilic acid, meta-arsanilic acid, or para-arsanilic acid.

The amount of phenyldiazonium salt added to the reaction mixture can and will vary. In certain embodiments, when carrier added arsenous acid is the starting material, the mole:mole ratio of the reaction intermediate to the phenyldiazonium salt may range from about 1:1 to about 1:20. In various embodiments, the molar ratio of reaction intermediate to the phenyldiazonium salt may range from about from about 1:1 to about 1:2, from about 1:2 to about 1:3, from about 1:3 to about 1:4, from about 1:4 to about 1:5, from about 1:5 to about 1:10, or from about 1:10 to about 1:20. In one exemplary embodiment, the mole:mole ratio of the reaction intermediate to phenyldiazonium salt may range from about 1:2 to about 1:4.

Specifically, when no-carrier added arsenic acid is the starting material, the mole:mole ratio of the reaction intermediate to the phenyldiazonium salt may range from about $1:10^6$ to about $1:10^{11}$. In various embodiments, the molar ratio of reaction intermediate to the phenyldiazonium salt may be about $1:10^6$, about $1:10^7$, about $1:10^8$, about $1:10^9$, about $1:10^{10}$, or about $1:10^{11}$. In other embodiments, the molar ratio of reaction intermediate to the phenyldiazonium salt may range from about $1:10^6$ to about $1:10^{10}$, about $1:10^6$ to about $1:10^9$, about $1:10^6$ to about $1:10^8$, about $1:10^6$ to about $1:10^7$, about $1:10^7$ to about $1:10^{11}$, about $1:10^7$ to about $1:10^{10}$, about $1:10^7$ to about $1:10^9$, about $1:10^7$ to about $1:10^8$, about $1:10^8$ to about $1:10^{11}$, about $1:10^8$ to about $1:10^{10}$, about $1:10^8$ to about $1:10^9$, about $1:10^9$ to about $1:10^{11}$, about $1:10^9$ to about $1:10^{10}$, or about $1:10^{10}$ to about $1:10^{11}$. In one exemplary embodiment, the mole:mole ratio of the reaction intermediate to phenyldiazonium salt may range from about $1:10^7$ to about $1:10^{10}$. In another exemplary embodiment, the mole:mole ratio of the reaction intermediate to phenyldiazonium salt may be about $1:10^7$.

The reaction is generally conducted in the presence of a solvent or solvent system. The solvent may be a polar protic solvent, a polar aprotic solvent, or a nonpolar organic solvent. Non-limiting examples of suitable polar protic solvents include methanol, ethanol, isopropanol, n-propanol, isobutanol, n-butanol, s-butanol, t-butanol, formic acid, acetic acid, water, and combinations thereof. Non-limiting examples of suitable polar aprotic solvents include acetone, acetonitrile, diethoxymethane, N,N-dimethylformamide (DMF), dimethyl sulfoxide (DMSO), N,N-dimethylpropanamide (or dimethylpropionamide; DMP), 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, N,N-dimethylacetamide (DMA), N-methyl-2-pyrrolidinone (NMP), 1,4-dioxane, ethyl formate, formamide, hexachloroacetone, hexamethylphosphoramide, methyl acetate, N-methylacetamide, N-methylformamide, methylene chloride, methoxyethane, morpholine, nitrobenzene, nitromethane, propionitrile, pyridine, sulfolane, tetramethylurea, tetrahydrofuran (THF), 2-methyl tetrahydrofuran, tetrahydropyran, trichloromethane, and combinations thereof. Representative nonpolar solvents include, but are not limited to, alkane and substituted alkane solvents (including cycloalkanes), aromatic hydrocarbons, esters, ethers, ketones, and combinations thereof. Specific nonpolar solvents that may be employed include, for example, benzene, butyl acetate, t-butyl methylether, t-butyl methylketone, chlorobenzene, chloroform, cyclohexane, dichloromethane, dichloroethane, diethyl ether, ethyl acetate, fluorobenzene, heptane, hexanes, methyl ethylketone (2-butanone), methyl isobutyl ketone, pentyl acetate, propyl acetates, toluene, and combinations thereof. In an exemplary embodiment, the solvent is a polar protic solvent. For example, the solvent is water and ethanol. In another exemplary embodiment, the solvent is a polar aprotic solvent. For example, the solvent is acetonitrile. In still another exemplary embodiment, the solvent is a combination of a polar protic solvent and a polar aprotic solvent. For example, the solvent is a combination of water and ethyl ether.

(d) Step B—Reaction Conditions

In general, the reaction is conducted at a temperature that ranges from about −20° C. to about 40° C. In various embodiments, the reaction may be conducted at a temperature from about −20° C. to about −10° C., from about −10° C. to about 0° C., from about 0° C. to about 10° C., from about 10° C. to about 20° C., from about 20° C. to about 30° C., or from about 30° C. to about 40° C. In an exemplary embodiment, the temperature is about −10° C. to about 10° C., such as about −5° C. to about 5° C., or about 0° C. In another exemplary embodiment, the temperature is from about 20° C. to about 30° C. The reaction generally is conducted in an inert atmosphere (e.g., under nitrogen or argon) and under ambient pressure.

In general, the reaction may proceed for about 1 minute to about 12 hours. Typically, the duration of the reaction is longer at lower reaction temperatures. In certain embodiments, the reaction may be allowed to proceed for about a period of time ranging from about 1 minute to about 5 minutes, from about 5 minutes to about 10 minutes, from about 10 minutes to about 15 minutes, from about 15 minutes to about 30 minutes, from about 30 minutes to about 1 hour, from about 1 hour to about 3 hours, from about 3 hours to about 6 hours, from about 6 hours to about 9 hours, or from about 9 hours to about 12 hours. In an exemplary embodiment, the reaction may be allowed to proceed for about a period of time ranging from about 30 minutes to about 1 hour.

In some embodiments, the phenylarsonic acid may be isolated from the reaction mixture using techniques known to those of skill in the art. Non-limiting examples of suitable techniques include precipitation, extraction, evaporation, distillation, chromatography, and crystallization. In an exemplary embodiment, the reaction mixture is neutralized and the phenylarsonic acid product is extracted.

The yield of the phenylarsonic acid can and will vary. Typically, the yield of the phenylarsonic acid may be at least about 40%. In one embodiment, the yield of the phenylarsonic acid may range from about 40% to about 60%. In another embodiment, the yield of the compound comprising phenylarsonic acid may range from about 60% to about 80%. In a further embodiment, the yield of the phenylarsonic acid may range from about 80% to about 90%. In still another embodiment, the yield of the phenylarsonic acid may be greater than about 90%, or greater than about 95%.

(e) Sulfur-Containing Compounds

A radiolabeled phenylarsonic acid may be used to prepare radiopharmaceuticals, such as dithiophenylarsenic compounds. For example, phenyl groups stabilize arsenic dithiol compounds. Successful labeling of phenylarsonic acid with a radioisotope of arsenic advances the development of arsenic radiopharmaceuticals. Radiolabeled arsenic complexes may be formed between reaction of an arsenic acid, such as phenylarsonic acid or para-arsanilic acid, and a sulfur-containing compound selected from monothiol and dithiol. In an exemplary embodiment, the phenylarsonic acid is first reacted with a monothiol, followed by reaction with either a monothiol or a dithiol. The result of this reaction includes compounds having Formula (I), (II), or (Ill) as described above in Section (I).

Non-limiting examples of monothiols include mercaptomethylamine, mercaptoethylamine, mercaptopropylamine, mercaptobutylamine, ammonium thioglycolate, cysteine, 2-aminoethanethiol (cysteamine), coenzyme A, and glutathione. Non-limiting examples of monothiols include methanethiol, ethanethiol, 1-propanethiol, 2-propanethiol, butanethiol, tert-butyl mercaptan, penanethiol, thiophenol, 2-mercaptoacetic acid, thioacetic acid, phenylmethanthiol (benzyl mercaptan), 2-mercaptoethanol, 3-mercaptopropane-1,2-diol, furan-2-ylmethanethiol, 2-mercaptoindole, and 2-(4-methylcyclohex-3-enyl)propane-2-thiol (thioterpineol). Non-limiting examples of dithiols include ethane-1,2-dithiol, 1,2-dimercaptosuccinic acid, 2,3-dimercaptosuccinic acid (DMSA), propane-1,3-dithiol, 6,8-dimercaptooctoic acid (thioctic acid), 1,5-dithiooctic acid, butane-1,4-dithiol, dithiothreitol, and dithioerythritol.

Non-limiting examples of the radiolabeled arsenic complexes include 1,2-dithioethanephenylarsine, 1,3-dithiopropanphenylarsine, (1,5-dithiooctic acid) phenylarsine, (1,2-dimercaptosuccinic acid) phenylarsine, 2-phenyl-1,3,2-dithiarsolane, 2-phenyl-1,3,2-dithiarsinane, 2-phenyl-1,3,2-dithiarsepane, 2-phenyl-1,3,2-dithiarsolane-4,5-dicarboxylic acid, 5-(2-phenyl-1,3,2-dithiarsinan-4-yl)pentanoic acid, 4-(1,3,2-dithiarsolan-2-yl)aniline, 2-(4-aminophenyl)-1,3,2-dithiarsolane-4,5-dicarboxylic acid, 4-(1,3,2-dithiarsinan-2-yl)aniline, and 5-(2-(4-aminophenyl)-1,3,2-dithioarsinan-4-yl)pentanoic acid and 2-(4-(methoxymethyl)phenyl)-1,3,2-dithiarsolane and other p-ethoxyphenylarsenic compounds.

An arsenic complex may be further derivatized with a biological vector, for example peptides such as bombesin or an antibody. Further examples of suitable biological vectors are described above in Section (I)(b).

(i) Step A

The amount of monothiol added to the reaction mixture can and will vary. Specifically, when no-carrier added arsenic acid is the starting material, the mole:mole ratio of the phenylarsonic acid to the monothiol may range from about $1:10^4$ to about $1:10^8$. In various embodiments, the molar ratio of phenylarsonic acid to the monothiol may be about $1:10^4$, about $1:10^5$, about $1:10^6$, about $1:10^7$, or about $1:10^8$. In other embodiments, the molar ratio of phenylarsonic acid to the monothiol may range from about $1:10^4$ to about $1:10^7$, about $1:10^4$ to about $1:10^6$, about $1:10^4$ to about $1:10^5$, about $1:10^5$ to about $1:10^8$, about $1:10^5$ to about $1:10^7$, about $1:10^5$ to about $1:10^6$, to about $1:10^6$ to about $1:10^8$, about $1:10^6$ to about $1:10^7$, or about $1:10^7$ to about $1:10^8$. In one exemplary embodiment, the mole:mole ratio of the phenylarsonic acid to the monothiol may range from about $1:10^5$ to about $1:10^7$. In another exemplary embodiment, the mole:mole ratio of the phenylarsonic acid to the monothiol may be about $1:10^6$.

In general, the reaction may be conducted at a temperature that ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100° C. to about 120° C. In an exemplary embodiment, the reaction may be conducted at a temperature of about 50° C. to about 70° C. In another exemplary embodiment, the reaction may be conducted at a temperature of about 60° C. The reaction generally is conducted in an inert atmosphere (e.g., under nitrogen or argon) and under ambient pressure.

Typically, the reaction is allowed to proceed for a sufficient period of time until the reaction is complete, as determined by chromatography (e.g., HPLC) or another suitable method. In this context, a "completed reaction" generally means that the reaction mixture contains a significantly diminished amount of starting material, and a significantly increased amount of reaction intermediate compared to the amounts of each present at the beginning of the reaction. In general, the reaction may proceed for about 1 minute to about 12 hours. Typically, the duration of the reaction is longer at lower reaction temperatures. In certain embodiments, the reaction may be allowed to proceed for a period of time ranging from about 1 minute to about 5 minutes, from about 5 minutes to about 10 minutes, from about 10 minutes to about 15 minutes, from about 15 minutes to about 30 minutes, from about 30 minutes to about 1 hour, from about 1 hour to about 3 hours, from about 3 hours to about 6 hours, from about 6 hours to about 9 hours, or from about 9 hours to about 12 hours. In an exemplary embodiment, the reaction may be allowed to proceed for a period of time ranging from about 30 minutes to about 1 hour.

(ii) Step B

The amount of sulfur-containing reagent (monothiol or dithiol) added to the reaction mixture can and will vary. In general, the mole:mole ratio of the phenylarsonic acid Step A to the sulfur-containing reagent may range from about 1:3 to about 1:30. In various embodiments, the molar ratio of the phenylarsonic acid to the sulfur-containing reagent may range from about 1:3 to about 1:4, from about 1:4 to about 1:5, from about 1:5 to about 1:10, from about 1:10 to about 1:20, or from about 1:20 to about 1:30.

Specifically, when no-carrier added arsenic acid is the starting material, the mole:mole ratio of the phenylarsonic acid Step A to the sulfur-containing reagent may range from about $1:10^5$ to about $1:10^9$. In various embodiments, the mole:mole ratio of the phenylarsonic acid Step A to the sulfur-containing reagent may be about $1:10^5$, about $1:10^6$, about $1:10^7$, about $1:10^8$, or about $1:10^9$. In other embodiments, the mole:mole ratio of the phenylarsonic acid Step A to the sulfur-containing reagent may range from about $1:10^5$ to about $1:10^8$, about $1:10^5$ to about $1:10^7$, about $1:10^5$ to about $1:10^6$, about $1:10^6$ to about $1:10^9$, about $1:10^6$ to about $1:10^8$, about $1:10^6$ to about $1:10^7$, about $1:10^7$ to about $1:10^9$, about $1:10^7$ to about $10^8$, or about $1:10^8$ to about $1:10^9$. In one exemplary embodiment, the mole:mole ratio of the phenylarsonic acid Step A to the sulfur-containing reagent may range from about $1:10^6$ to about $1:10^8$. In another exemplary embodiment, the mole:mole ratio of the phenylarsonic acid Step A to the sulfur-containing reagent may be about $1:10^7$.

In general, the reaction may be conducted at a temperature that ranges from about 0° C. to about 120° C. In various embodiments, the reaction may be conducted at a temperature from about 0° C. to about 20° C., from about 20° C. to about 40° C., from about 40° C. to about 60° C., from about 60° C. to about 80° C., from about 80° C. to about 100° C., or from about 100° C. to about 120° C. In an exemplary embodiment, the reaction may be conducted at a temperature from about 20° C. to about 40° C. In another exemplary embodiment, the temperature is from about 20° C. to about 30° C. The reaction generally is conducted in an inert atmosphere (e.g., under nitrogen or argon) and under ambient pressure.

In general, the reaction may proceed for about 1 minute to about 12 hours. Typically, the duration of the reaction is longer at lower reaction temperatures. In certain embodiments, the reaction may be allowed to proceed for about a period of time ranging from about 1 minute to about 5 minutes, from about 5 minutes to about 10 minutes, from about 10 minutes to about 15 minutes, from about 15 minutes to about 30 minutes, from about 30 minutes to about 1 hour, from about 1 hour to about 3 hours, from about 3 hours to about 6 hours, from about 6 hours to about 9 hours, or from about 9 hours to about 12 hours. In an exemplary embodiment, the reaction may be allowed to proceed for about 0.5 hours to about 1.5 hours. In another exemplary embodiment, the reaction may be allowed to proceed for about 0.5 hours to about 1 hour.

The yield of the arsenic complex can and will vary. Typically, the yield of the arsenic complex may be at least about 40%. In one embodiment, the yield of the arsenic complex may range from about 40% to about 60%. In another embodiment, the yield of the arsenic complex may range from about 60% to about 80%. In a further embodiment, the yield of arsenic complex may range from about 80% to about 90%. In still another embodiment, the yield of arsenic complex may be greater than about 90%, or greater than about 95%.

DEFINITIONS

The compounds described herein have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxly group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "oxygen-protecting group" as used herein denotes a group capable of protecting an oxygen atom (and hence, forming a protected hydroxyl group), wherein the protecting group may be removed, subsequent to the reaction for which protection is employed, without disturbing the remainder of the molecule. Exemplary oxygen protecting groups include ethers (e.g., allyl, triphenylmethyl (trityl or Tr), p-methoxybenzyl (PMB), p-methoxyphenyl (PMP)), acetals (e.g., methoxymethyl (MOM), 3-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of oxygen protecting groups and the synthesis thereof may be found in "Protective Groups in Organic Synthesis" by T. W. Greene and P. G. M. Wuts, $3^{rd}$ ed., John Wiley & Sons, 1999.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples are included to demonstrate certain embodiments of the invention. It should be appreciated by those of skill in the art that the techniques disclosed in the examples represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth is to be interpreted as illustrative and not in a limiting sense.

Example 1

Phenyldiazonium Tetrafluoroborate—Method A

Sodium tetrafluoroborate ($NaBF_4$, 6.7 g, 61 mmol) was added to a 100-mL round-bottomed flask in an ice-water bath. Deionized water (18Ω, 30 mL) and concentrated hydrochloric acid (HCl, 16 mL) were added. The solution was cooled and rapidly stirred. Aniline (5 mL, 55 mmol) was added and the solution cooled for 30 minutes. Meanwhile, a solution of sodium nitrite ($NaNO_2$) was prepared by dissolving 3.8 g (55 mmol) in 6 mL of water and cooled on an ice-water bath. The nitrile solution was added dropwise to the round-bottomed flask over a period of 20 minutes. The solution was allowed to react for about 5 minutes, resulting in a nearly white precipitant. The precipitant was filtered and washed sequentially with 95% ethanol and diethyl ether, yielding 5.7 grams (55%). The product was stored in a freezer until use.

Example 2

Phenyldiazonium Tetrafluoroborate—Method B

A solution of sodium nitrite (0.833 g, 1.67 mL) was slowly added to a stirring mixture of aniline (1.0 g) and 48% fluoroboric acid ($HBF_4$, 5.55 mL) cooled to 0° C. Following addition of the sodium nitrite, the reaction mixture was stirred for 10 more minutes and then filtered. The precipitant was washed sequentially with 48% fluoroboric acid, 95% ethanol, and a copious amount of diethyl ether. The initial yield was 61%, and additional product was obtained from the filtrate. The combined product was stored in a desiccator until use.

Example 3

Phenylarsonic Acid

At a temperature of about 50° C., a supersaturated stock solution (2.83 M) of sodium carbonate ($Na_2CO_3$) was prepared in deuterium oxide ($D_2O$). A stock of copper(II) sulfate ($CuSO_4$) solution (1.21 M) was also prepared in $D_2O$.

In a vessel 0.200 mL of the $Na_2CO_3$ solution (0.566 mmol) was combined with 0.300 mL of $D_2O$ and 22.3 mg of arsenic trioxide ($As_2O_3$, 16.3 mg of As, 225 µmol) and heated to about 90° C. with stirring until the arsenic trioxide dissolved. The $CuSO_4$ solution (66 µL, 80 µmol was added. The combined solution was allowed to stir at 90° C. for about 10 minutes. The solution was transferred to an ice-water bath and allowed to equilibrate to a temperature of 0° C. A solution of phenyldiazonium tetrafluoroborate (127.9 mg, 666 µmol), a mole:mole ratio of 3:1 diazonium/arsenic) in 1.5 mL $D_2O$ was also prepared, cooled to 0° C. with stirring and added to the arsenic-containing solution. The solution was filtered and a 0.500 mL $D_2O$ rinse of reaction flask was also passed through the filter. The filter was washed with $D_2O$ (twice with 0.300 mL and once with 0.200 mL). Concentrated HCl (94 µL, 1.14 mmol) was added to the filtrate to neutralize the carbonate. The solution was then filtered through a 0.22-µm filter. A clear light yellow precipitate formed after filtration. The phenylarsonic acid was identified through $^1$H-NMR and mass spectrometry.

Example 4

Radiolabeled $^{76}$As-Phenylarsonic Acid

Carrier added arsenic-76 was obtained from the University of Missouri Research Reactor and behaved analogously to arsenic-72 and arsenic-77. About 2.35 mg of $^{76}$As-labeled As$_2$O$_3$ (1.78 mg As, 23.8 μmol) in 0.1 mL of aqueous 2 M sodium carbonate (Na$_2$CO$_3$) was added to 0.5 mL of aqueous 2 M Na$_2$CO$_3$ in a two-necked round-bottomed flask (1200 μmol total). This solution was heated in an oil bath at 80° C. to ensure complete dissolution of arsenic trioxide. A solution of aqueous copper(II) sulfate (CuSO$_4$, 37 μL, 1.61 M, 60 μmol) was added to the flask and the solution was allowed to cool to room temperature before it was transferred to an ice bath. A slurry of 0.1035 g of phenydiazonium tetrafluoroborate (0.540 mmol) in 1 mL water and 0.25 mL ethanol also at 0° C. was added to the flask in five equal portions of 0.25 mL each at four-minute intervals. An additional 0.25 mL water was also added after four more minutes. The green solution turned dark brown upon the first addition of the diazonium salt. After the additions, the solution was filtered to remove a brown precipitate. The filtrate was neutralized with 0.15 mL concentrated hydrochloric acid (HCl) and filtered through a 0.22-micron filter. The phenylarsenous acid was observed by high-performance liquid chromatography (HPLC) with ultraviolet (UV) detection at 254 nm. A radiation detector at the same elution time showed a clear signal for the $^{76}$As analog. A yield of about 18% was observed for the $^{76}$As-phenylarsonic acid product.

Example 5

Radiolabeled $^{77}$As-Phenylarsonic Acid and $^{77}$As-Dithioglycolylphenylarsine No-carrier-added arsenic, as $^{77}$As-arsenate, in methanol was separated from a neutron-irradiated, enriched $^{76}$GeO$_2$ target. The target had been dissolved in 2 M KOH, neutralized with concentrated HCl, diluted in methanol, and passed through three methanol prewetted Waters CE Plus Accell short Sep-Pak™ cartridges (360 mg each) arranged in tandem and fitted with a 0.2-μm Whatman filter disc, and eluted with 10 mL of methanol. The methanol was removed under a gentle stream of air. Deionized water (18Ω, 0.9 mL) and ammonium thioglycolate (5.5 M, 0.1 mL) were added to the residue, which was then heated to 60° C. for 50 minutes while stirring. Phenyldiazonium tetrafluoroborate (153.0 mg, 79.7 mmol) was added as a solid, vortexed for 30 seconds, and then ethyl ether (2 mL) and water (18Ω, 1 mL) were added. The aqueous phase was separated, filtered through a 0.2-μm Whatman filter disc prior to injection onto an HPLC for analysis.

An aliquot (0.2 mL) was analyzed by reversed phase HPLC on a Phenomenex Luna Phenyl-Hexyl column (3μ, 100×4.6 mm) using a Shimadzu HPLC system with UV-vis detection at 254 nm and 280 nm, and radioactivity detection on a Beckman 170 radioisotope detector. A gradient elution system at a flow rate of 0.5 mL/min was used (3 minutes at pH 2.75 phosphate buffer, a linear gradient to 70/30 pH 2.75 phosphate buffer/acetonitrile over 8 minutes, to 40/60 over 9 minutes, and finally to 20/80 over 5 minutes). The $^{77}$As-phenylarsonic acid labeled preparation described above eluted with a retention time of 13.89 minutes, while the non-radioactive standard compound eluted at 13.63 minutes. This 0.25-minute time difference is attributed to the time between the two detectors. An additional $^{77}$As-labeled compound was observed with a retention time of approximately 33 minutes. The identity of this second species may be dithioglycolylphenylarsine the desired phenyl arsenic acid with two thioglycolic acid groups replacing the two hydroxyl groups or possibly the diphenylarsonic acid analogue.

Example 6

Synthesis of No Carrier added $^{77}$As p-ethoxyphenyl-1,2-ethanedithiolatoarsine Radioactivity in the form of $^{77}$AsO$_4^{3-}$ in methanol ($^{77}$As stock solution, 500 μL, 2.1 mCi, 2.6×10$^{-11}$ mol or ~2 ng) was obtained from the University of Missouri Research Reactor (MURR). Acetonitrile (650 μL) was added to the screw cap vial containing 250 μL of the $^{77}$As stock solution (1.05 mCi, 1.3×10$^{-11}$ mol, ~1 ng). Ammonium mercaptoacetate (50 μL of 500 mM) was added and the reaction mixture stirred in a 60° C. water bath for 0.5 h. The reduction of $^{77}$AsO$_4^{3-}$(V) to $^{77}$As(mercaptoacetate)$_3$ was complete as determined by radioactive TLC (silica gel, R$_f$=0.64 in 9% acetone in methanol). A 5 μL aliquot of Cu$^0$ nanoparticle solution (Strem Chemicals, Inc., <20 nm in acetone at 100 mg/ml as provided (surfactant and reactant-free)) was added, followed by 100 μL of p-ethoxybenzenediazonium tetrafluoroborate (0.1 mg/μL) in acetonitrile. The reaction mixture was removed from the water bath and the reaction continued at room temperature for 45 min. The reaction mixture was then evaluated by radioactive TLC; [$^{77}$As]p-ethoxyphenylarsonic acid was produced as determined by radioactive TLC (silica gel, R$_f$=0.24 in 9% acetone in methanol). Ammonium mercaptoacetate (10 μL of 5.5 M) was added and the reaction mixture was placed in a 60° C. water bath 45 min. The reduction of [As$^{77}$]p-ethoxyphenylarsonic acid was then confirmed by radioactive TLC (silica gel, R$_f$=0.44 in 9% acetone in methanol). Ethanedithiol (10 μL; 1.123 g/mL) was added and the reaction mixture stirred at room temperature for 30 min. The radiochemical yield of $^{77}$As p-ethoxyphenyl-1,2-ethanedithiolatoarsine was determined to be 95% by radioactive TLC (silica gel, R=0.72 in 9% acetone in methanol). The TLC plates were dried before scanning for radioactivity using a gas proportional detector (Bioscan). Non-radioactive standards were used for identification of the various species.

What is claimed is:

1. A method of producing radiolabeled phenylarsonic acid, the method comprising:
   (a) contacting a radiolabeled no-carrier added arsenic acid with a monothiol to form a first solution; and
   (b) contacting the first solution with a copper-based catalyst and a phenyldiazonium salt to give a second solution comprising the radiolabeled phenylarsonic acid.

2. The method of claim 1, wherein the radiolabeled no-carrier added arsenic acid is chosen from H$_3$AsO$_4$ or AsO$_4^{3-}$.

3. The method of claim 1, wherein the arsenic is $^{77}$As or $^{72}$As.

4. The method of claim 1, wherein the monothiol is ammonium thioglycolate.

5. The method of claim 1, wherein the mole:mole ratio of the no-carrier added arsenic acid to monothiol ranges from about 1:10$^5$ to about 1:10$^7$.

6. The method of claim 1, wherein the first solution is heated to about 50° C. to about 70° C.

7. The method of claim 1, wherein step (a) is allowed to proceed for a period of time ranging from about 30 minutes to about 1 hour.

8. The method of claim 1, wherein the phenyldiazonium salt is tetrafluoroborate salt.

9. The method of claim 1, wherein the phenyldiazonium salt is ethoxybenzendiazonium salt.

10. The method of claim 1, wherein the mole:mole ratio of the reaction intermediate from step (a) to phenyldiazonium salt ranges from about $1:10^7$ to about $1:10^{10}$.

11. The method of claim 1, wherein the copper-based catalyst is copper(0) nanoparticles.

12. The method of claim 1, wherein the copper-based catalyst is copper(0) nanoparticles; and the mole to mole ratio of the reaction intermediate from step (a) to copper(0) nanoparticles ranges from about $1:10^5$ to about $1:10^6$.

13. The method of claim 1, wherein step (b) is conducted at about 20° C. to about 30° C.

14. The method of claim 1, wherein step (b) is allowed to proceed for a period of time ranging from about 30 minutes to about 1 hour.

15. The method of claim 1, wherein the radiolabeled phenylarsonic acid is further reacted with a monothiol and a monothiol or dithiol.

16. The method of claim 15, wherein the monothiol is ammonium thioglycolate.

17. The method of claim 15, wherein the mole:mole ratio of the radiolabeled phenylarsonic acid to the monothiol ranges from about $1:10^5$ to about $1:10^7$.

18. The method of claim 15, wherein the dithiol is ethane-1,2-dithiol.

19. The method of claim 15, wherein the mole:mole ratio of the radiolabeled phenylarsonic acid to the dithiol ranges from about $1:10^6$ to about $1:10^8$.

20. The method of claim 1, wherein the radiolabeled phenylarsonic acid is 2-(4-(methoxymethyl)phenyl)-1,3,2-dithiarsolane.

* * * * *